(12) United States Patent
De Nijs et al.

(10) Patent No.: US 7,323,454 B2
(45) Date of Patent: *Jan. 29, 2008

(54) ETONOGESTREL ESTERS

(75) Inventors: Henrik H De Nijs, Oss (NL); Hendrikus Adrianus Antonius H.A.A. Van Der Voort, Oss (NL); Dirk D. Leysen, Oss (NL); Arij Jan A.J. Grootenhuis, Oss (NL)

(73) Assignee: N.V. Organon, Oss (NL)

( * ) Notice: Subject to any disclaimer, the term of this patent is extended or adjusted under 35 U.S.C. 154(b) by 215 days.

This patent is subject to a terminal disclaimer.

(21) Appl. No.: 10/516,402

(22) PCT Filed: May 22, 2003

(86) PCT No.: PCT/EP03/50187

§ 371 (c)(1),
(2), (4) Date: Nov. 30, 2004

(87) PCT Pub. No.: WO03/102012

PCT Pub. Date: Dec. 11, 2003

(65) Prior Publication Data

US 2005/0222113 A1 Oct. 6, 2005

(30) Foreign Application Priority Data

May 30, 2002 (EP) .................. 02077119

(51) Int. Cl.
*A61K 31/56* (2006.01)
*C07J 1/00* (2006.01)

(52) U.S. Cl. .................. 514/179; 552/526

(58) Field of Classification Search ......... 514/179; 552/526

See application file for complete search history.

(56) References Cited

FOREIGN PATENT DOCUMENTS

| AU | 687013 | 3/1994 |
|---|---|---|
| DE | 1013284 | 8/1957 |
| DE | 4240806 A1 | 6/1994 |
| DE | 196 13 698 A | 1/1997 |
| EP | 0 129 947 A2 | 1/1985 |
| EP | 0 737 477 A | 10/1996 |
| GB | 845442 | 8/1960 |
| WO | WO 94 04157 | 3/1994 |
| WO | WO 97 03709 | 2/1997 |
| WO | WO 99 67270 | 12/1999 |
| WO | WO 99 67271 | 12/1999 |
| WO | WO 00 42942 | 7/2000 |
| ZA | 9606083 | 7/1996 |

OTHER PUBLICATIONS

Guerin, J.F. et al., "Inhibition of spermatogenesis in men using various combinations of oral progestagens . . . " International Journal of Andrology (1988) pp. 187-199.
Machine translation of DE 4240806 A1, 1994.
Database WPI, Week 199524, Derwent Publications Ltd., London, GB; AN 1995-182895, XP-002265978 & JP 07 101884 A (Sekisui Chem Ind. Co. Ltd) (Apr. 1995).
Johnson, A., "Aliphatic Esters of 6,6-Difluoro-17β-Hydroxy-17-Ethynyl-4-Estren-3-One (6,6-Difluoronorethindrone) and (±)-6,6-Difluoro-13β-Ethyl-17βHydorxy-17-Ehtynyl-4-Gonen-3-One ((±)-6,6-Difluoronorgestrel)," *Steroids* 20 (1972) 263-267.
McPhail et.al., "The assay of progestin," *J. of Physiology* 83, (1934) 145-156.
Shafiee et.al., "Long-Acting Contraceptive Agents: Aliphatic and Alicyclic Carboxylic Esters of Levonorgestrel," *Steroids* 41 (1983) 349-359.
Watson et al., "Long-Acting Contraceptive Agents: Esters of Norethiserone with α and/or β-Chain Branching." *Steroids* 41 (1983) 255-265.
Wu et al., "Oral Progestogen Combined with Testosterone as a Potential Male Contraceptive," *J. Clin. Endocrinol. Metab.* 84 (1999) 112-122.

*Primary Examiner*—Barbara P. Badio
(74) *Attorney, Agent, or Firm*—Susan Hess

(57) ABSTRACT

The subject invention provides new progestogen esters and uses thereof.

11 Claims, 3 Drawing Sheets

Etonogestrel heptanoate
(Etonogestrel enanthate)

Etonogestrel nonanoate

Etonogestrel decanoate

Etonogestrel undecanoate

Etonogestrel dodecanoate

Etonogestrel tridecanoate

Etonogestrel pentadecanoate

C7: Etonogestrel heptanoate
C9: Etonogestrel nonanoate
C10: Etonogestrel decanoate
C11: Etonogestrel undecanoate
C12: Etonogestrel dodecanoate
C13: Etonogestrel tridecanoate

ETONOGESTREL ESTERS

This application is the 35 U.S.C. §371 filing of PCT/EP03/050187 filed May 22, 2003.

FIELD OF THE INVENTION

The subject invention concerns the field of (female and male) contraception, (female and male) hormone replacement therapy (HRT) and treatment/prevention of gynaecological disorders.

BACKGROUND

Contraceptive methods for men and women are important for worldwide reproductive health.

However, no effective and efficient methods of male contraception are as of yet available.

Male contraception seeks to suppress spermatogenesis through the suppression of the gonadotropins luteinizing hormone (LH) and follicle-stimulating hormone (FSH). This results in a depletion of intratesticular testosterone and cessation of spermatogenesis.

Administration of progestagen results in a dose dependent suppression of pituitary gonadotrophins and consequently, a decrease in testosterone levels and a reversible inhibition of spermatogenesis. An exogenous androgen. is required to compensate for the reduced testosterone levels. In the same way, male HRT can be accomplished, resulting in replacement of testosterone by an exogenous androgen which is safer on the prostate than endogenous testosterone.

The use of progestogens together with androgens for use as male contraceptives is known (Guerin and Rollet (1988), International Journal of Andrology 11, 187-199).

However, the use of specific esters of etonogestrel for male contraception and male HRT has not been suggested.

In addition, the use of progestogens together with estrogens for use in female contraception is known (M. Tausk, J. H. H. Thijssen, Tj. B. van Wimersma Greidanus, "Pharmakologie der Hormone", Georg Thieme Verlag, Stuttgart, 1986).

Progestagens are widely used for female contraception and in female HRT. In contraception, the combination progestagen-estrogen oral contraceptives are the most widely used. Administration of such a combination results in a number of effects: it blocks ovulation, it interferes with phasic development of the endometrium which decreases the chance for successful implantation, and it causes the cervical mucus to become so viscous that it hinders sperm penetration. Most progestagen-only-pills (POP's) aim at the last mentioned effect only.

Female HRT is aimed at suppletion of endogenous estrogen for the treatment of peri- and postmenopausal complaints (hot flushes, vaginal dryness), and for prevention of symptoms of long-term estrogen deficiency. The latter include osteoporosis, coronary artery disease, urogenital incontinence, and possibly also Alzheimer's disease and colorectal cancer. A drawback of long-term unopposed estrogen administration is the associated increase in endometrium proliferation, which in turn may increase the risk of endometrial cancer. For that reason, progestagens are co-administered in long-term regimes, because of their ability to reduce the proliferative activity of endometrial epithelium and to induce secretory conversion.

However, the use of specific esters of etonogestrel for female contraception, female HRT and treatment/prevention of gynaecological disorders has not been suggested.

The subject invention describes new esters of etonogestrel, i.e. etonogestrel decanoate, etonogestrel undecanoate, and etonogestrel dodecanoate which have surprisingly been found to have a better pharmacokinetic profile than other etonogestrel esters. These esters enable a single-dose administration of a progestogen with a long duration of action.

The subject invention provides new progestogen esters, i.e. etonogestrel decanoate, etonogestrel undecanoate, and etonogestrel dodecanoate and uses thereof for both male and female contraception and male and female HRT.

In addition, the use of these esters for treatment and prevention of female gynaecological disorders such as endometriosis, menorrhagia, meno-metrorrhagia, pre-menstrual syndrome and dysmenorrhoea are also contemplated.

Figure 1:
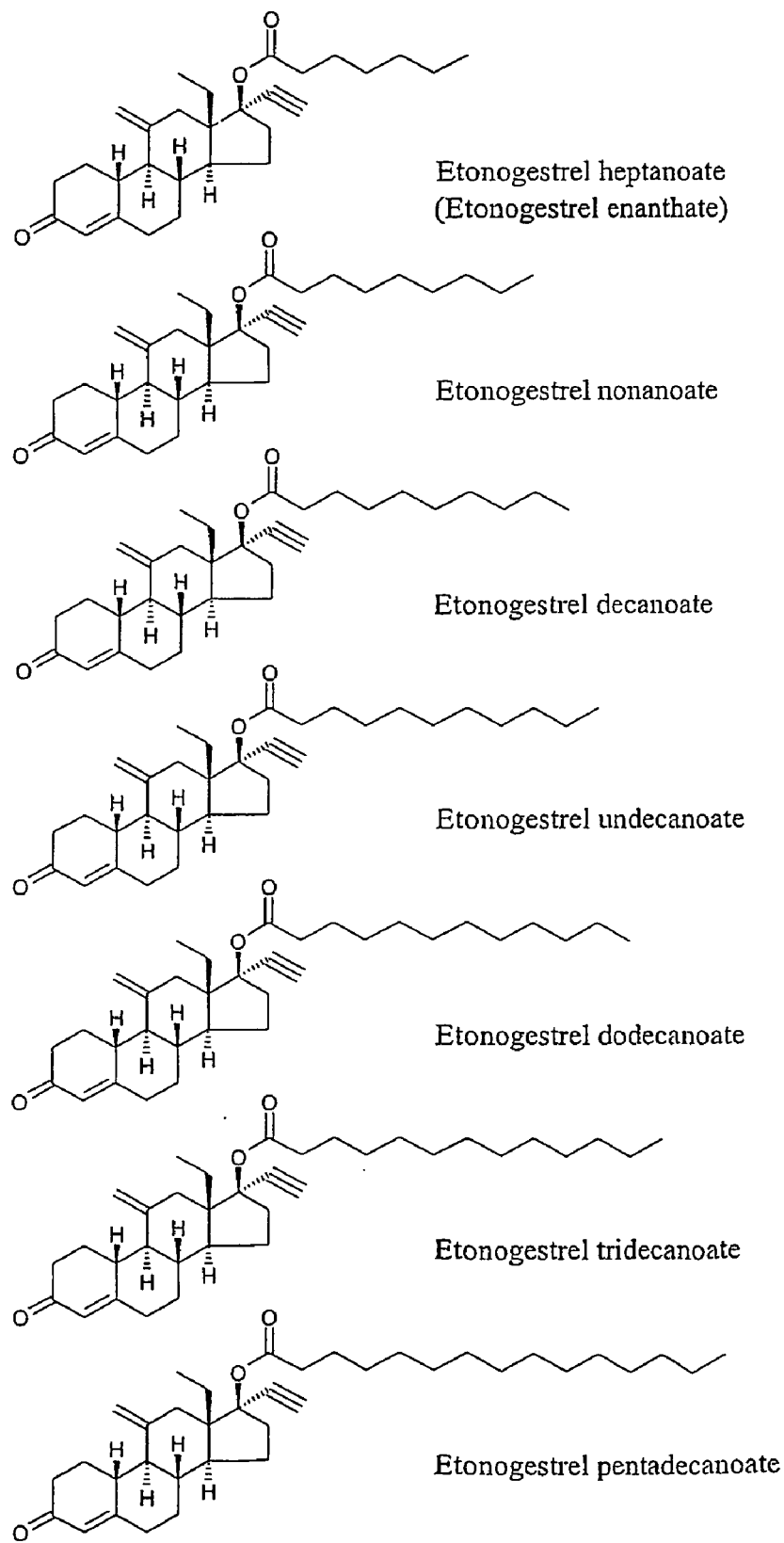
FIG. 1

Chemical structures of etonogestrel heptanoate (etonogestrel enanthate), etonogestrel nonanoate, etonogestrel decanoate, etonogestrel undecanoate, etonogestrel dodecanoate, etonogestrel tridecanoate, and etonogestrel pentadecanoate.

FIG. 2a

Effect of one intramuscular (IM) injection of etonogestrel, etonogestrel heptanoate (etonogestrel, enanthate), etonogestrel noncanoate and etonogestrel undecanoate on plasma levels of etonogestrel in male intact rabbits. Means and SEM of N=3.

FIG. 2b

Effect of one intramuscular (IM) injection of etonogestrel heptanoate (etonogestrel enanthate), etonogestrel nonanoate, etonogestrel decanoate, etonogestrel undecanoate, etonogestrel dodecanoate, etonogestrel tridecanoate on plasma levels of etonogestrel in male intact rabbits. Means and SEM of N=3.

DETAILED DESCRIPTION OF THE INVENTION

The subject invention provides the compounds etonogestrel decanoate, etonogestrel undecanoate, and etonogestrel dodecanoate. The subject invention contemplates a contraceptive and/or HRT kit comprising a contraceptively and/or therapeutically effective amount of etonogestrel decanoate and/or etonogestrel undecanoate and/or etonogestrel dodecanoate for both male and female contraception and HRT.

The subject invention further provides a use of a contraceptively and/or therapeutically effective amount of etonogestrel decanoate and/or etonogestrel undecanoate and/or etonogestrel dodecanoate for the preparation of a medicament for contraception and/or HRT. In a preferred embodiment, the medicament is for male contraception and/or male HRT. In another embodiment, the medicament is for female contraception and/or female HRT.

The subject invention further contemplates a method of contraception and/or HRT comprising administering to a subject a contraceptively and/or therapeutically effective amount of etonogestel decanoate and/or etonogestrel undecanoate and/or etonogestrel dodecanoate. In a preferred embodiment, the subject is a male subject. In another embodiment, the subject is a female subject.

The subject invention additionally provides a use of a therapeutically effective amount of etonogestrel decanoate and/or etonogestrel undecanoate and/or etonogestrel dodecanoate for the preparation of a medicament for the treatment and/or prevention of female gynaecological disorders such as endometriosis, menorrhagia, meno-metrorrhagia, pre-menstrual syndrome and dysmenorrhoea.

The subject invention further contemplates a method of treatment and/or prevention of female gynaecological disorders such as endometriosis, menorrhagia, meno-metrorrhagia, pre-menstrual syndrome and dysmenorrhoea comprising administering to a female subject a therapeutically effective amount of etonogestrel decanoate and/or etonogestrel undecanoate and/or etonogestrel dodecanoate.

The compounds of the subject invention can be administered via any suitable route available to the skilled person. In the case of oral administration, a solid dosage unit such as a tablet or a capsule is contemplated. The compounds of the invention can be formulated with a pharmaceutically acceptable carrier, such as described in the standard reference, Gennaro et al, *Remmington: The Science and Practice of Pharmacy*, (20th ed., Lippincott Williams & Wilkins, 2000, see especially Part 5: Pharmaceutical Manufacturing). The compounds of the invention and the pharmaceutically acceptable carrier may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. nasal spray. For making dosage units, e.g. tablets, the use of conventional additives such as fillers, colorants, polymeric binders, lubricants, flow enhancers, glidants and the like is contemplated. In general any pharmaceutically acceptable additive which does not interfere with the function of the active compounds can be used. The compounds of the invention may also be included in an implant, a vaginal ring, a patch, a gel, and the like.

Suitable carriers with which the compositions can be administered include lactose, starch, cellulose derivatives and the like, or mixtures thereof used in suitable amounts.

The dose of and regimen of administration of the compounds of the invention, or a pharmaceutical composition thereof, to be administered will depend on the therapeutic effect to be achieved and will vary with the route of administration, and the age and condition of the individual subject to whom the medicament is to be administered, and/or the particular contraceptive or HRT regimen in which it is used. Typical dosage amounts are 0.001-5 mg per kg body weight.

The present invention is further described in the following example which is not in any way intended to limit the scope of the invention as claimed.

EXAMPLE

Kinetics of Etonogestrel C7, C9, C10, C11, C12 and C13 Esters in Rabbits

The following etonogestrel esters were prepared and tested in rabbits:
Etonogestrel heptanoate
Etonogestrel nonanoate
Etonogestrel decanoate
Etonogestrel undecanoate
Etonogestrel dodecanoate
Etonogestrel tridecanoate
Etonogestrel pentadecanoate was also prepared.
FIG. 1 shows the chemical structure of these compounds. As a reference, etonogestrel was also included.

Preparation of Etonogestrel Esters

General methodology for the preparation of esters from alcohols can be found in e.g. Greene, T. W. et al, "Protective groups in organic synthesis", John Wiley & Sons, NY, 1999 (third edition). Preparation of esters from tertiary alcohols (like etonogestrel) can be accomplished by several techniques, for instance:

1) tertiary alcohol, carboxylic acid, trifluoroacetic acid-anhydride, DE 1013284 (1956); 2) tertiary alcohol, acid chloride, pyridine, Watson, T. G. et al, Steroids 41, 255 (1983); 3) tertiary alcohol, acid chloride, TlOEt, Shafiee, A. et al, Steroids 41, 349 (1983), 4) tertiary alcohol, carboxylic acid-anhydride, TsOH, benzene, Johnson, A. L., Steroids, 20, 263 (1972); and 5) tertiary alcohol, carboxylic acid-anhydride, DMAP, $CH_2Cl_2$, Shafiee, A. et al, Steroids 41, 349 (1983).

Preparation of (17α)-13-Ethyl-11-methylene-17-[[(1-oxononyl)oxy]-18,19-dinorpregn-4-en-20-yn3-one (Etonogestrel Nonanoate)

a) A solution of nonanoic acid (1.95 g) in dry toluene (8 ml) was cooled to 0° C. and treated with trifluoroacetic acid anhydride (2.6 g). After 30 min. stirring, (17α)-13-ethyl-17-hydroxy-11-methylene-18,19-dinorpregn-4-en-20-yn-3-one (etonogestrel, 2.0 g) in dry toluene (15 ml) was added and the reaction mixture was stirred for 17 h at room temperature. The reaction mixture was washed with water, a saturated aqueous solution of sodium hydrogen carbonate, water, and reduced pressure. The residue was purified by column chromatography (toluene/ethyl acetate 95:5). The product (2.08 g) was dissolved in ethyl acetate (40 ml), cooled to 0° C., and stirred with aqueous sodium hydroxide (1 M, 13 ml) for 2 h. The mixture was extracted with ethyl acetate; the combined organic phases were washed with ice-cold aqueous sodium hydroxide (1 M), water and brine, dried and concentrated under reduce pressure. Column chromatography afforded (17α)-13-ethyl-11-methylene-17-[[(1-oxononyl)oxy]-18,19-dinorpregn-4-en-20-yn-3-one (1.25 g). $^1$H-NMR ($CDCl_3$): δ5.89 (m, 1H), 5.08 (bs, 1H), 4.85 (bs, 1H), 2.82 (ddd, 1H, J=14.8, 9.5 and 6.3 Hz), 2.73 (d, 1H, J=12.8 Hz), 2.69-219 (m), 2.63 (s, 1H), 2.11 (m, 1H), 1.90-1.21 (m), 1.15 (m, 1H), 1.05 (t,3H, J=7.5 Hz), 0.88 (t, 3H, J=7.1 Hz). Measured mass $[M+H]^+$ 465.3358. Calculated mass $[M+H]^+$ 465.3363.

In a manner analogous to the procedure described above, etonogestrel heptanoate, etonogestrel decanoate, etonogestrel undecanoate, etonogestrel dodecanoate, etonogestrel tridecanoate, and etonogestrel pentadecanoate were prepared:

b) (17α)-13-Ethyl-11-methylene-17-[[(1-oxoheptyl)oxy]-18,19-dinorpregn-4-en-20-yn-3 - one (etonogestrel heptanoate). $^1$H-NMR ($CDCl_3$): δ5.89 (m, 1H), 5.08 (bs, 1H), 4.85 (bs, 1H), 2.82 (ddd, 1H, J=14.8, 9.5 and 6.3 Hz), 2.73 (d, 1H, J=12.6 Hz), 2.68-2.19 (m), 2.63 (s, 1H), 2.11 (m, 1H), 1.90-1.24 (m), 1.15 (m, 1H), 1.05 (t, 3H, J=7.5 Hz), 0.89 (t, 3H, J=7.1 Hz). Measured mass $[M+H]^+$ 437.3027. Calculated mass $[M+H]^+$ 437.3050.

c) (17α)-13-Ethyl-11-methylene-17-[[(1-oxodecyl)oxy]-18,19-dinorpregn-4-en-20-yn-3 -one (etonogestrel decanoate). $^1$H-NMR ($CDCl_3$): δ5.89 (bs, 1H), 5.08 (bs, 1H), 4.84 (bs, 1H), 2.82 (m, 1H), 2.73 (d, 1H, J=12.6 Hz), 2.67-2.18 (m), 2.63 (s, 1H), 2.11 (m, 1H), 1.90-1.21 (m), 1.15 (m, 1H), 1.06 (t, 3H, J=7.5 Hz), 0.88 (t, 3H, J=7.1 Hz). Measured mass [M+H]$^+$ 479.3508. Calculated mass [M+H]$^+$ 479.3519.

d) (17α)-13-Ethyl-11-methylene-17-[[(1-oxoundecyl)oxy]-18,19-dinorpregn-4-en-20-yn-3-one (etonogestrel undecanoate). $^1$H-NMR (CDCl$_3$): δ5.89 (m, 1H), 5.08 (bs, 1H), 4.85 (bs, 1H), 2.82 (ddd, 1H, J=14.8, 9.5 and 6.3 Hz), 2.73 (d, 1H, J==7.5 Hz), 0.88 (t, 3H, J=7.1 Hz). Measured mass [M+H]$^+$ 493.3664. Calculated mass [M+H]$^+$ 493.3676.

e) (17α)-13-Ethyl-11-methylene-17-[[(1-oxododecyl)oxy]-18,19-dinorpregn-4-en-20-yn-3-one (etonogestrel dodecanoate). $^1$H-NMR (CDCl$_3$): δ5.89 (bs, 1H), 5.08 (bs, 1H), 4.85 (bs, 1H), 2.82 (m, 1H), 2.73 (d, 1H, J=12.6 Hz), 2.65-2.18 (m), 2.64 (s, 1H), 2.11 (m, 1H), 1.90-1.20 (m), 1.15 (m, 1H), 1.06 (t, 3H, J=7.5 Hz), 0.88 (t, 3H, J=7.1 Hz). Measured mass [M+H]$^+$ 507.3829. Calculated mass [M+H]$^+$ 507.3832.

f) (17α)-13-Ethyl-11-methylene-17-[[(1-oxotridecyl)oxy]-18,19-dinorpregn-4-en-20-yn-3-one (etonogestrel tridecanoate). $^1$H-NMR (CDCl$_3$): δ5.89 (bs, 1H), 5.08 (bs, 1H), 4.85 (bs, 1H), 2.82 (m, 1H), 2.73 (d, 1H, J=12.6 Hz), 2.65-2.18 (m), 2.64 (s, 1H), 2.11 (m, 1H), 1.90-1.20 (m), 1.15 (m, 1H), 1.06 (t, 3H, J=7.5 Hz), 0.89 (t, 3H, J=7.1 Hz). Measured mass [M+H]$^+$ 521.4007. Calculated mass [M+H]$^+$ 521.3989.

g) (17α)-13-Ethyl-11-methylene-17-[[(1-oxopentadecyl)oxy]-18,19-dinorpregn-4-en-20-yn-3-one (etonogestrel pentadecanoate). $^1$H-NMR (CDCl$_3$): δ5.89 (bs, 1H), 5.08 (bs, 1H), 4.85 (bs, 1H), 2.82 (m, 1H), 2.73 (d, 1H, J=12.6 Hz), 2.65-2.19 (m), 2.63 (s, 1H), 2.11 (m, 1H), 1.90-1.20 (m), 1.15 (m, 1H), 1.06 (t, 3H, J=7.5 Hz), 0.89 (t, 3H, J=7.1 Hz). Measured mass [M+H]$^+$ 549.4278. Calculated mass [M+H]$^+$ 549.4302.

Pharmacokinetics Studies in the Rabbit

For the determination of the pharmacokinetic profile of the different etonogestrel-esters after parenteral application, i.m. application in the castrated rabbit model was chosen instead of s.c. Briefly, rabbits were injected once (day 1) with indicated etonogestrel-esters at 20 mg/kg in arachis oil (with a concentration of 40 mg/ml). At day 1, 2, 3, 4, 5, 6, 7, 8, 10, 12, 14, 21, 28, 35, 49, 63, 77, 92, 106, 120 and 133 blood was collected from the ear arteria, in EDTA-containing tubes. EDTA plasma was prepared (1500 g, 15 min) and stored at −20° C. With LC-MSMS the amount of parent compound (etonogestrel) was determined in these samples. The lower limit of this new assay is 0.5 nmol/l, from 0-250 nmol/l a linear curve was obtained with a correlation coefficient of 0,9998.

Figure 2A:
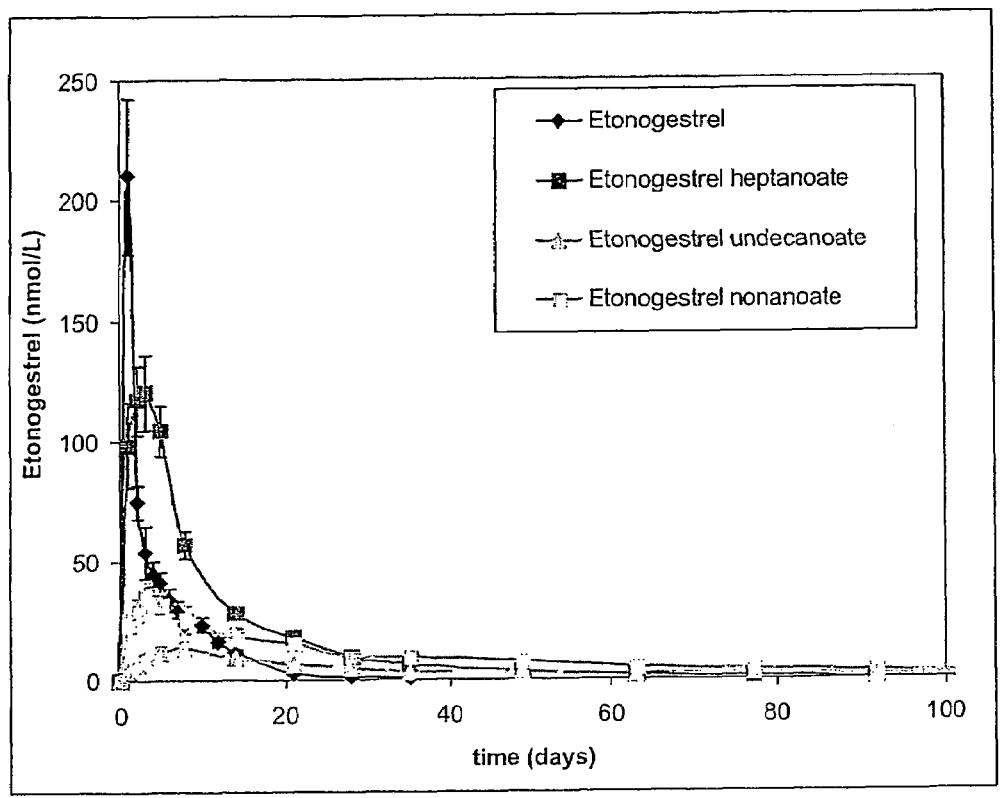
Figure 2A:
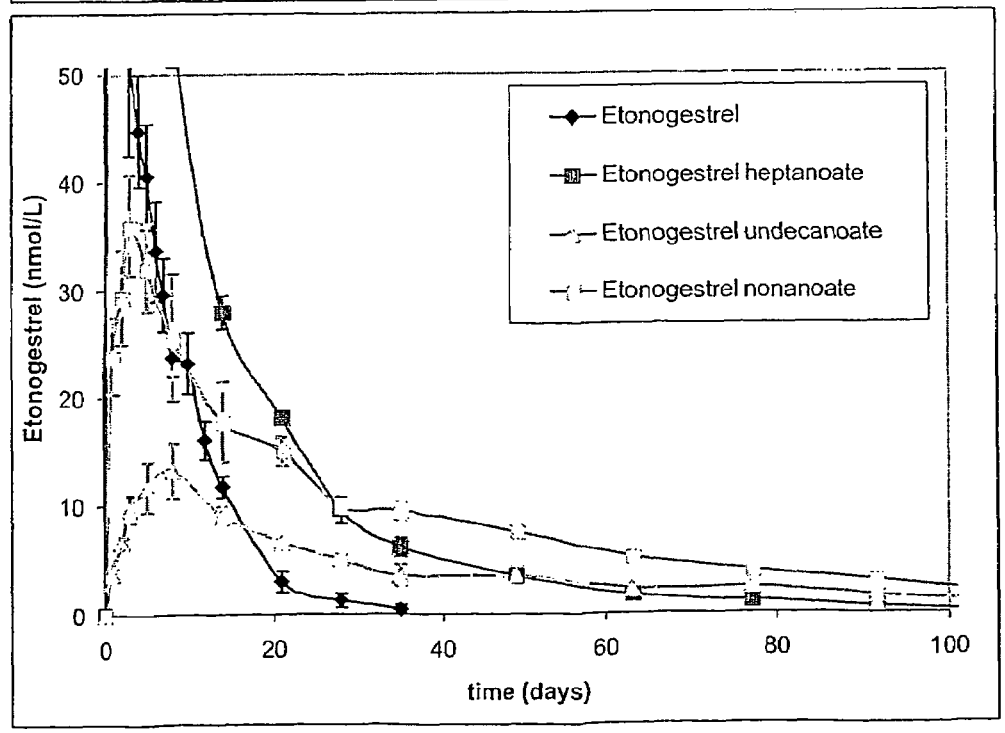

As shown in FIG. 2a, etonogestrel itself resulted in very high peak levels (200 nmol/l), which declined in 28 days to levels of etonogestrel below 1 nmol/l. Etonogestrel-heptanoate also gave rise to high initial peak levels of etonogestrel (120 nmol/l). Etonogestrel nonanoate gave lower peak levels and extended duration with serum levels of etonogestrel above 1 nmol/l. As compared to the other two esters in FIG. 2a, etonogestrel undecanoate gave the most optimal balance between initial peak levels (maximum of 13 nmol/l after eight days) and duration of action (more than 92 days above 1 nmol/l).

Figure 2B:
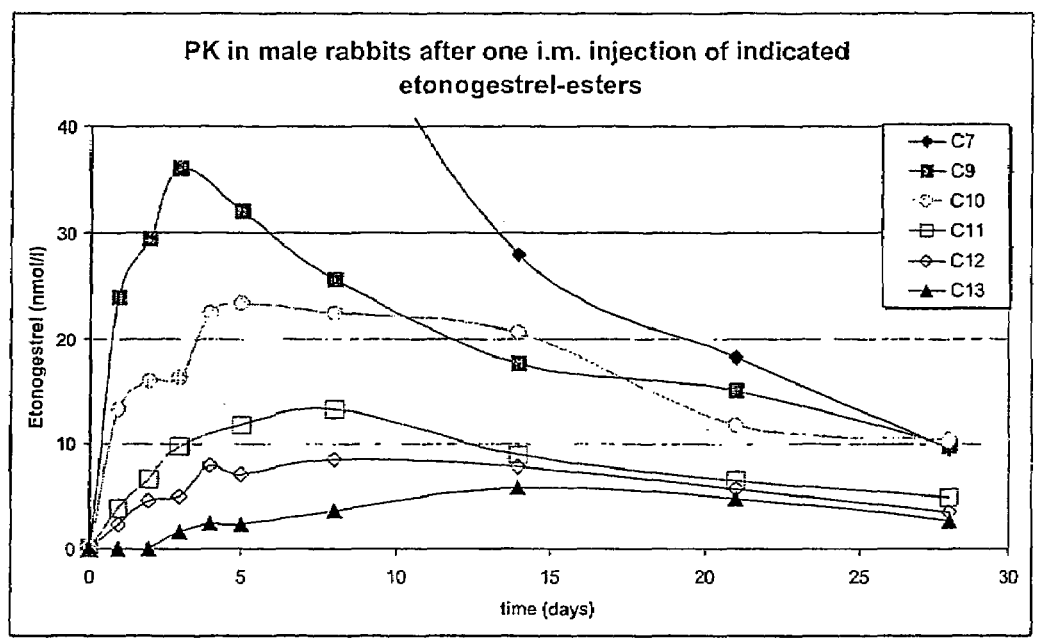

As shown in FIG. 2b, etonogestrel decanoate gave an initial peak level of 24 nmol/l after 5 days whereas etonogestrel dodecanoate gave an initial peak level of 9 nmol/l after 8 days. With etonogestrel tridecanoate, no initial levels of etonogestrel were observed.

From FIGS. 2a and 2b, it can be seen that preferred etonogestrel esters are etonogestrel decanoate, etonogestrel undecanoate, and etonogestrel dodecanoate.

The invention claimed is:
1. Etonogestrel undecanoate.
2. Etonogestrel decanoate.
3. Etonogestrel dodecanoate.
4. A contraceptive and/or HRT kit comprising a contraceptively and/or therapeutically effective amount of etonogestrel undecanoate and/or etonogestrel decanoate and/or etonogestrel dodecanoate.
5. The kit according to claim 4 for male contraception and/or male HRT.
6. The kit according to claim 4 for female contraception and/or female HRT.
7. A method of contraception and/or HRT, comprising:
administering to a subject a contraceptively and/ar therapeutically effective amount of etonogestrel undecanoate and/or etonogestrel decanoate and/or etonogestrel dodecanoate.
8. The method according to claim 7, wherein the subject is a male subject.
9. The method according to claim 7, wherein the subject is a female subject.
10. A method of treating a female gynecological disorder, comprising:
administering to a female subject a therapeutically effective amount of etonogestrel undecanoate and/or etonogestrel decanoate and/or etonogestrel dodecanoate effective to treat the disorder.
11. The method according to claim 10, wherein the female gynecological disorder is selected from the group consisting of endometriosis, menorrhagia, meno-metrorrhagia, premenstrual syndrome and dysmenorrhoea.

* * * * *

UNITED STATES PATENT AND TRADEMARK OFFICE
CERTIFICATE OF CORRECTION

| | | |
|---|---|---|
| PATENT NO. | : 7,323,454 B2 | Page 1 of 1 |
| APPLICATION NO. | : 10/516402 | |
| DATED | : January 29, 2008 | |
| INVENTOR(S) | : Henrik H. de Nijs et al. | |

It is certified that error appears in the above-identified patent and that said Letters Patent is hereby corrected as shown below:

Claim 7: Col. 6, lines 32-36;

A method of contraception and/or HRT, comprising:

administering to a subject a contraceptively ~~and/or~~ therapeutically effective amount of etonogestrel undecanoate and/or etonogestrel decanoate and/or etonogestrel dodecanoate.

should read

A method of contraception and/or HRT, comprising:

administering to a subject a contraceptively and/or therapeutically effective amount of etonogestrel undecanoate and/or etonogestrel decanoate and/or etonogestrel dodecanoate.

Signed and Sealed this

Thirteenth Day of May, 2008

JON W. DUDAS
*Director of the United States Patent and Trademark Office*